(12) United States Patent
Yoneyama

(10) Patent No.: US 11,943,522 B2
(45) Date of Patent: Mar. 26, 2024

(54) MANUFACTURING METHOD OF IMAGE PICKUP APPARATUS FOR ENDOSCOPE, IMAGE PICKUP APPARATUS FOR ENDOSCOPE, AND ENDOSCOPE

(71) Applicant: OLYMPUS CORPORATION, Tokyo (JP)

(72) Inventor: Jumpei Yoneyama, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 259 days.

(21) Appl. No.: 17/375,174

(22) Filed: Jul. 14, 2021

(65) Prior Publication Data

US 2021/0344822 A1    Nov. 4, 2021

Related U.S. Application Data

(63) Continuation of application No. PCT/JP2019/001257, filed on Jan. 17, 2019.

(51) Int. Cl.
*H04N 23/55* (2023.01)
*A61B 1/00* (2006.01)
(Continued)

(52) U.S. Cl.
CPC ......... *H04N 23/55* (2023.01); *G02B 23/2484* (2013.01); *H01L 27/1462* (2013.01);
(Continued)

(58) Field of Classification Search
CPC ...... H04N 23/55; H04N 23/54; H04N 23/555; G02B 23/2484; G02B 7/025; G02B 7/02;
(Continued)

(56) References Cited

U.S. PATENT DOCUMENTS

| 2016/0133762 A1* | 5/2016 | Blasco Claret ...... H04N 25/134 438/69 |
| 2018/0324337 A1 | 11/2018 | Yoshikawa et al. |
| 2020/0004039 A1* | 1/2020 | Ogasahara ............. H04N 23/00 |

FOREIGN PATENT DOCUMENTS

| CN | 108351485 A | 7/2018 |
| JP | 2010-103493 A | 5/2010 |

(Continued)

OTHER PUBLICATIONS

International Search Report dated Feb. 19, 2019 issued in PCT/JP2019/001257.

*Primary Examiner* — Nasim N Nirjhar
(74) *Attorney, Agent, or Firm* — Scully, Scott, Murphy & Presser, P.C.

(57) ABSTRACT

A manufacturing method of an image pickup apparatus for endoscope includes manufacturing an optical member in which a plurality of optical devices are stacked, and an image pickup member including an image pickup device having a light receiving surface, measuring a position of an image-forming plane on which an object image, light of which is focused by the optical member, is formed, and fixing the optical member and the image pickup member in a state where an interval is adjusted so that a measured position of the image-forming plane becomes a position of the light receiving surface by performing curing processing on a transparent resin disposed to fill an optical path between the optical member and the image pickup member.

16 Claims, 9 Drawing Sheets

(51) Int. Cl.
  *G02B 23/24* (2006.01)
  *H01L 27/146* (2006.01)
  *H04N 23/50* (2023.01)
  *H04N 23/54* (2023.01)

(52) U.S. Cl.
  CPC .. *H01L 27/14685* (2013.01); *H01L 27/14687* (2013.01); *H04N 23/54* (2023.01); *A61B 1/0011* (2013.01); *H04N 23/555* (2023.01)

(58) Field of Classification Search
  CPC ........... H01L 27/1462; H01L 27/14685; H01L 27/14687; H01L 21/02; H01L 27/14618; H01L 27/14625; A61B 1/0011; A61B 1/051; G03B 17/02
  See application file for complete search history.

(56) References Cited

FOREIGN PATENT DOCUMENTS

| | | |
|---|---|---|
| WO | 2014/203800 A1 | 12/2014 |
| WO | 2017/072985 A1 | 5/2017 |
| WO | 2017/203593 A1 | 11/2017 |
| WO | 2018/198266 A1 | 11/2018 |
| WO | 2019/138639 A1 | 7/2019 |

* cited by examiner

MANUFACTURING METHOD OF IMAGE PICKUP APPARATUS FOR ENDOSCOPE, IMAGE PICKUP APPARATUS FOR ENDOSCOPE, AND ENDOSCOPE

CROSS REFERENCE TO RELATED APPLICATION

This application is a continuation application of PCT/JP2019/001257 filed on Jan. 17, 2019, the entire contents of which are incorporated herein by this reference.

BACKGROUND OF THE INVENTION

1. Field of the Invention

The present invention relates to a manufacturing method of an image pickup apparatus for endoscope including an optical member in which a plurality of optical devices are stacked and an image pickup member including an image pickup device, the image pickup apparatus for endoscope including the optical member in which the plurality of optical devices are stacked and the image pickup member including the image pickup device, and the endoscope including the image pickup apparatus for endoscope including the optical member in which the plurality of optical devices are stacked and the image pickup member including the image pickup device.

2. Description of the Related Art

Making a diameter of an image pickup apparatus for endoscope to be disposed at a rigid distal end portion of an endoscope smaller is important to achieve a less-invasive endoscope. Examples of a method for efficiently manufacturing an optical portion of the image pickup apparatus can include a wafer level method in which a stacked optical wafer is manufactured by stacking a plurality of optical wafers each including a plurality of optical devices, and the stacked optical wafer is cut into pieces of a plurality of optical members. The optical member manufactured using the wafer level method is referred to as a wafer level optical portion.

Japanese Patent Application Laid-Open Publication No. 2010-103493 discloses an image pickup apparatus including a wafer level optical member and an image pickup member.

For example, an optical wafer including a resin lens manufactured through resin molding is inexpensive and can be easily manufactured.

SUMMARY OF THE INVENTION

A manufacturing method of an image pickup apparatus for endoscope of embodiments includes manufacturing an optical member in which a plurality of optical devices are stacked and an image pickup member including an image pickup device having a light receiving surface, measuring a position of an image-forming plane on which an object image, light of which is focused by the optical member, is formed, stacking the optical member and the image pickup member, adjusting an interval between the optical member and the image pickup member so that a measured position of the image-forming plane becomes a position of the light receiving surface, and fixing the optical member and the image pickup member in a state of the adjusted interval by performing curing processing on a transparent resin disposed to fill an optical path between the optical member and the image pickup member.

An image pickup apparatus for endoscope of another embodiment is manufactured by a manufacturing method of an image pickup apparatus for endoscope including manufacturing an optical member in which a plurality of optical devices are stacked and an image pickup member including an image pickup device having a light receiving surface, measuring a position of an image-forming plane on which an object image, light of which is focused by the optical member, is formed, stacking the optical member and the image pickup member, adjusting an interval between the optical member and the image pickup member so that a measured position of the image-forming plane becomes a position of the light receiving surface, and fixing the optical member and the image pickup member in a state of the adjusted interval by performing curing processing on a transparent resin disposed to fill an optical path between the optical member and the image pickup member.

An image pickup apparatus for endoscope of still another embodiment includes an optical member in which a plurality of optical devices are stacked, an image pickup member including an image pickup device having a light receiving surface, and a transparent resin which fills an optical path between the optical member and the image pickup member, and an interval between the optical member and the image pickup member is fixed by the transparent resin in a state where an object image, light of which is focused by the optical member, is formed on the light receiving surface.

An endoscope of yet another embodiment includes an image pickup apparatus for endoscope which includes an optical member in which a plurality of optical devices are stacked, an image pickup member including an image pickup device having a light receiving surface, and a transparent resin which fills an optical path between the optical member and the image pickup member, and in which an interval between the optical member and the image pickup member is fixed by the transparent resin in a state where an object image, light of which is focused by the optical member, is formed on the light receiving surface.

DETAILED DESCRIPTION OF THE PREFERRED EMBODIMENTS

<Endoscope>

Figure 1:
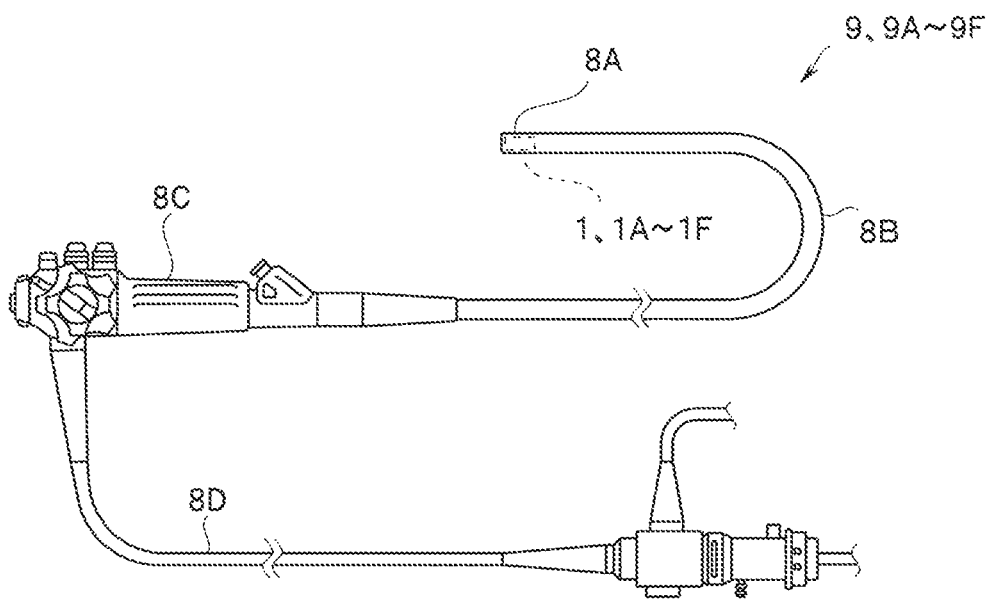
FIG. 1 is an external view of an endoscope of embodiments.

As illustrated in FIG. 1, endoscopes 9, 9A to 9F of embodiments of the present invention includes an insertion portion 8B in which image pickup apparatuses 1, 1A to 1F for endoscope (hereinafter, also referred to as "image pickup apparatuses 1, 1A to 1F") are disposed at a rigid distal end portion 8A, an operation portion 8C disposed on a base end side of the soft insertion portion 8B, and a universal cord 8D extending from the operation portion 8C. The image pickup apparatus 1 is disposed at the distal end portion 8A of the insertion portion 8B of the endoscope 9, and outputs an image pickup signal. The image pickup signal outputted from the image pickup apparatus 1 is transmitted to a processor by way of a cable which allows insertion of the universal cord 8D. A drive signal from the processor to the image pickup apparatus 1 is also transmitted by way of the cable which allows insertion of the universal cord 8D.

As will be described later, the image pickup apparatuses 1, 1A to 1F have a small external size in an optical axis orthogonal direction, have high performance, and can be easily manufactured. Thus, less-invasive and high-performance endoscopes 9, 9A to 9F can be easily manufactured. Note that the endoscopes 9, 9A to 9F may be rigid endoscopes and can be applied to medical use or industrial use.

First Embodiment

Figure 2:
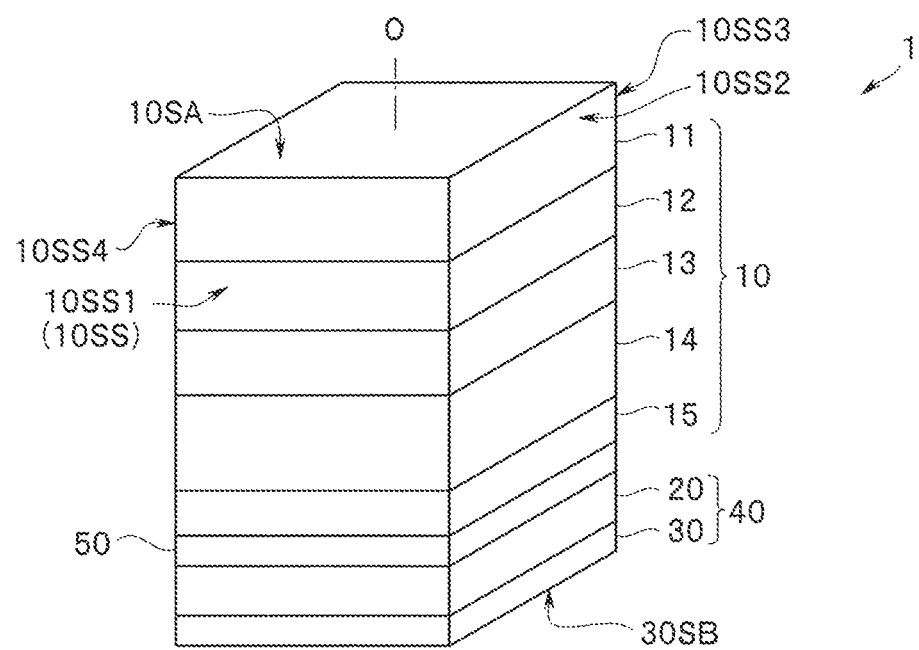
FIG. 2 is a perspective view of an image pickup apparatus for endoscope of a first embodiment.
Figure 3:
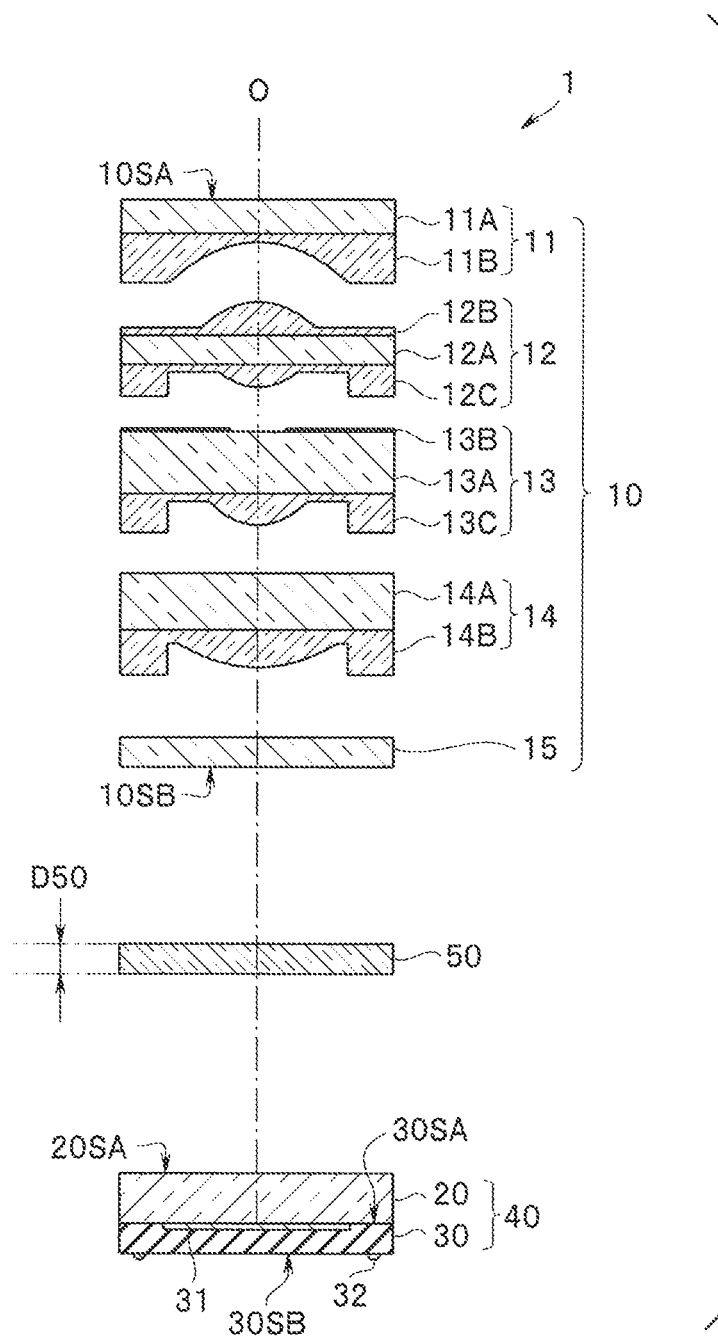
FIG. 3 is an exploded cross-sectional diagram of the image pickup apparatus for endoscope of the first embodiment.

As illustrated in FIG. 2 and FIG. 3, the image pickup apparatus 1 for endoscope of the present embodiment includes an optical member 10, an image pickup member 40, and a resin 50 which is an adhesive agent.

In the following description, the drawings based on the respective embodiments are schematically illustrated. Relationships between thicknesses and widths of each portion, ratios of thicknesses of respective portions, relative angles, and the like, are different from actual relationships, ratios, relative angles, and the like. Some relationships of dimensions and ratios may be different between the drawings. Illustration of some components may be omitted.

The optical member 10 is a stacked optical system in which a plurality of optical devices 11 to 15 are stacked. The optical member 10 has a rectangular parallelepiped shape having an entrance surface 10SA, an exit surface 10SB facing the entrance surface 10SA, and four side surfaces 10SS (10SS1, 10SS2, 10SS3 and 10SS4).

The optical device 11 includes a glass plate 11A and a resin lens 11B. The optical device 12 includes a glass plate 12A and resin lenses 12B and 12C. The optical device 13 includes a glass plate 13A, an aperture 13B and a resin lens 13C. The optical device 14 includes a glass plate 14A and a resin lens 14B. The optical device 15 is an infrared cut filter device having a function of blocking infrared light. In other words, the optical devices 11 to 14 are hybrid lens devices in which resin lenses which are formed with a resin and which have aspheric surfaces are disposed on the glass plates. A configuration of the optical member 10 is designed in accordance with specifications of the image pickup apparatus.

The image pickup member 40 includes an image pickup device 30 having a light receiving surface 30SA and a back surface 30SB facing the light receiving surface 30SA. A cover glass 20 which protects the light receiving surface 30SA is bonded on the light receiving surface 30SA using a transparent resin (not illustrated). An upper surface 20SA of the cover glass 20 faces the light receiving surface 30SA and the back surface 30SB of the image pickup device 30, and the upper surface 20SA, the light receiving surface 30SA and the back surface 30SB have the same external sizes in the optical axis orthogonal direction as external sizes of the entrance surface 10SA and the exit surface 10SB. Note that the image pickup member 40 may be the image pickup device 30 to which the cover glass 20 is not bonded.

The image pickup device 30 includes a light receiving member 31 formed with a CCD, or the like, on the light receiving surface 30SA, and includes an external electrode 32 connected to the light receiving member 31 on the back surface 30SB facing the light receiving surface 30SA. The image pickup device 30 may be either a surface irradiation type image sensor or a backside irradiation type image sensor.

The resin 50 is disposed between the exit surface 10SB of the optical member 10 and the upper surface 20SA of the cover glass 20 of the image pickup member 40. The resin 50 is a transparent ultraviolet curable resin which fills an optical path between the optical member 10 and the image pickup member 40. The uncured resin 50 in a liquid state is disposed between the optical member 10 and the image pickup member 40. Then, the resin 50 is subjected to curing processing by irradiation of ultraviolet light in a state where a thickness is adjusted. In other words, a thickness D50 of the resin 50 is adjusted so that an object image, light of which is focused by the optical member 10, is formed on the light receiving surface 30SA.

As will be described later, the optical member 10 is a wafer level optical portion manufactured by cutting a stacked wafer 10W (see FIG. 5) in which a plurality of optical wafers respectively including a plurality of optical devices are stacked and bonded using an adhesive agent, and thus, the optical member 10 can be easily manufactured. Note that the four side surfaces 10SS of the optical member 10 which is a wafer level optical member are cut surfaces.

As already described above, the optical member 10 which is a wafer level optical member has a focal length different for each stacked wafer. However, in the image pickup apparatus 1 which is manufactured using a manufacturing method which will be described later, a position of the image-forming plane of the optical member 10 matches a position of the light receiving surface 30SA of the image pickup member 40, so that high performance can be achieved, and a favorable image can be obtained.

<Manufacturing Method>

Figure 4:
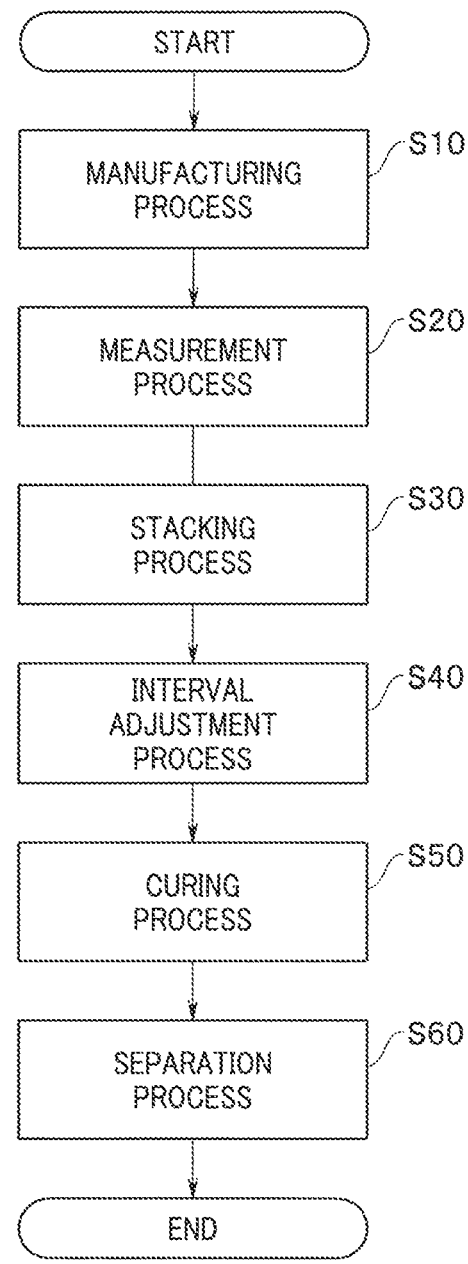
FIG. 4 is a flowchart of a manufacturing method of the image pickup apparatus for endoscope of the first embodiment.

A manufacturing method of the image pickup apparatus 1 will be described next along a flowchart illustrated in FIG. 4.

<Step S10> Manufacturing Process

Figure 5:
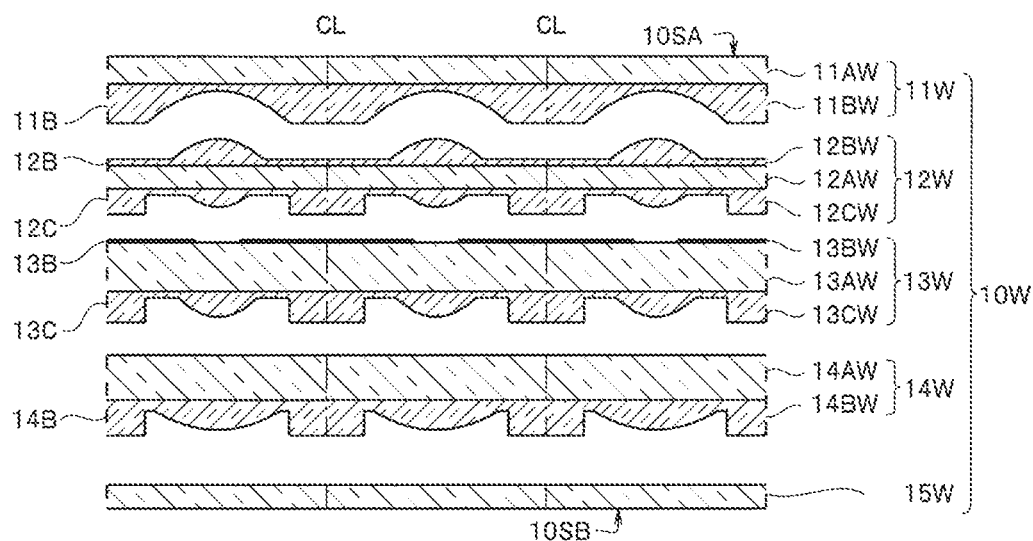
FIG. 5 is a cross-sectional diagram for explaining the manufacturing method of the image pickup apparatus for endoscope of the first embodiment.

As illustrated in FIG. 5, a stacked optical wafer 10W is manufactured by optical wafers 11W to 15W being stacked and bonded. Note that in FIG. 5 and the like, lines indicated with reference numeral CL are cut lines in a separation process S60.

In the optical wafer 11W, a lens layer 11BW including a plurality of resin lenses 11B is disposed on a glass wafer 11AW. In the optical wafer 12W, a lens layer 12BW including a plurality of resin lenses 12B and a lens layer 12CW including a plurality of resin lenses 12C are disposed on a glass wafer 12AW. In the optical wafer 13W, an aperture layer 13BW including a plurality of apertures 12B and a lens layer 13CW including a plurality of resin lenses 13C are disposed on a glass wafer 13AW. In the optical wafer 14W, a lens layer 14BW including a plurality of resin lenses 14B is disposed on a glass wafer 14AW.

The lens layer 11BW, the lens layer 12BW, the lens layer 12CW, the lens layer 13CW and the lens layer 14BW are disposed by, for example, applying a transparent resin for a lens, pressing a mold having a predetermined shape against the transparent resin for the lens, and curing the transparent resin for the lens by irradiating the transparent resin with ultraviolet light (UV). In other words, the resin lens is formed using a mold.

Note that in place of the lens layer 11BW connected to the plurality of resin lenses 11B, for example, a plurality of separated resin lenses 11B may be disposed on the glass wafer 11AW.

The optical wafer 15W is an infrared cut filter wafer.

Although not illustrated, alignment marks are respectively disposed at outer peripheral portions of the optical wafers 11W to 15W, and the optical wafers 11W to 15W are stacked in a state where the optical wafers 11W to 15W are positioned on the basis of the alignment marks. Further, the stacked optical wafer 10W is manufactured by the optical wafers 11W to 15W being bonded using an ultraviolet curable adhesive which is disposed in advance and which is not illustrated.

Meanwhile, a plurality of light receiving members 31 are formed on the light receiving surface 30SA of the semiconductor wafer using a publicly-known semiconductor manufacturing technology. An image pickup wafer 40W is manufactured by the cover glass wafer 20W being bonded to the light receiving surface 30SA (see FIG. 7). A transparent resin wafer may be used in place of the cover glass wafer 20W. In other words, a member which protects the light receiving surface 30SA is not limited to the cover glass wafer 20W (cover glass 20), but may be a resin plate as long as the resin plate is transparent.

<Step S20> Measurement Process

Figure 6:
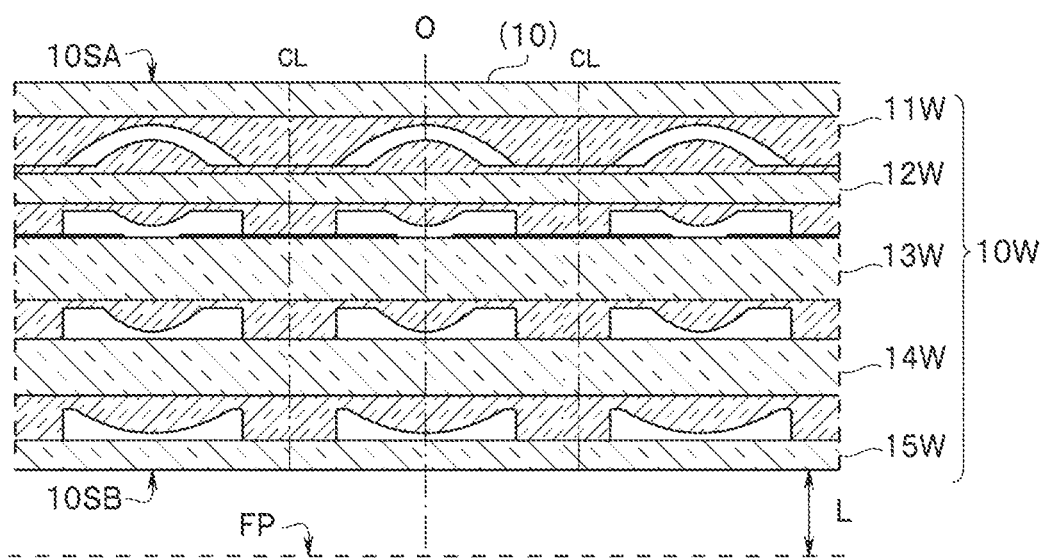
FIG. 6 is a cross-sectional diagram for explaining the manufacturing method of the image pickup apparatus for endoscope of the first embodiment.

As illustrated in FIG. 6, a position of an image-forming plane FP is measured, the image-forming plane FP being a plane on which an object image, light of which is focused by the optical member 10 included in the stacked optical wafer 10W, is formed.

Figure 7:
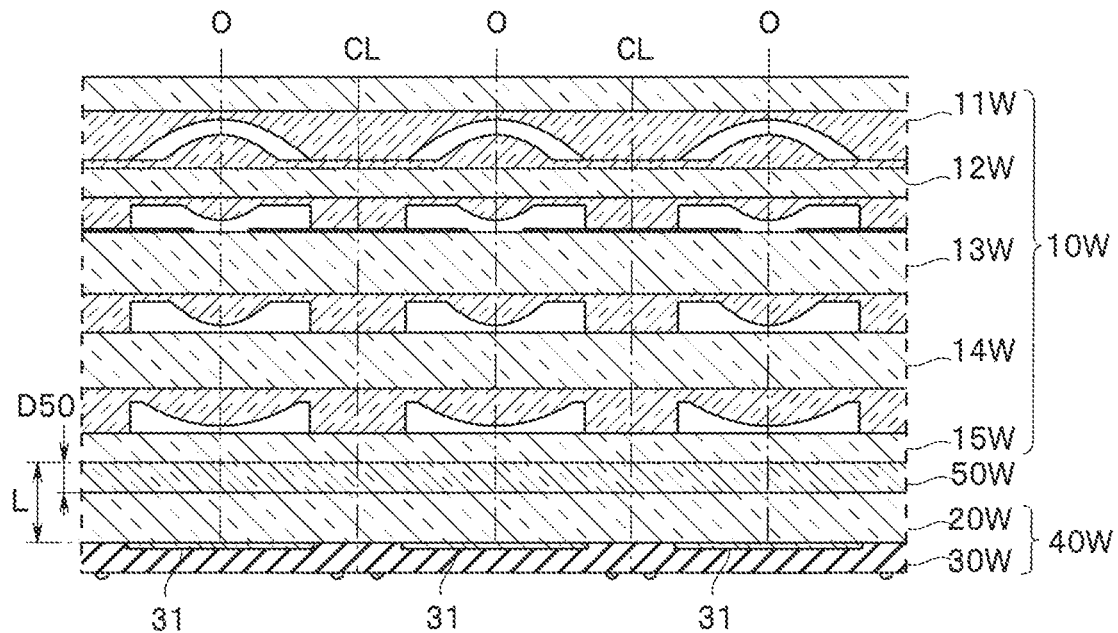
FIG. 7 is a cross-sectional diagram for explaining the manufacturing method of the image pickup apparatus for endoscope of the first embodiment.

Note that as illustrated in FIG. 7, in the manufacturing method of the image pickup apparatus 1, the cover glass wafer 20W is disposed between the exit surface 10SB of the stacked optical wafer 10W and the light receiving surface 30SA of the semiconductor wafer 30W, and further, the resin 50W is disposed. Thus, the method preferably further includes a correction process of correcting the measured position of the image-forming plane FP in view of a refractive index, or the like, as well as thicknesses of the cover glass wafer 20W and the resin 50W. More strictly, a transparent resin (not illustrated) which bonds the cover glass 20 on the light receiving surface 30SA is also disposed between the exit surface 10SB and the light receiving surface 30SA, and thus, correction may be performed in the correction process in view of a thickness, a refractive index, or the like, of the transparent resin (not illustrated).

For example, the position of the image-forming plane FP, that is, a length L from the exit surface 10SB to the image-forming plane FP is actually measured by a measurement light being incident from the entrance surface 10SA of the stacked optical wafer 10W.

The plurality of optical members 10 included in one stacked optical wafer 10W have substantially the same length L from the exit surface 10SB to the image-forming plane FP. It is therefore only necessary to perform measurement for one optical member 10 among the plurality of optical members 10.

<Step S30> Stacking Process

As illustrated in FIG. 7, the stacked optical wafer 10W and the image pickup wafer 40W are disposed at an interval, and the resin 50W is disposed between the stacked optical wafer 10W and the image pickup wafer 40W. The resin 50W which is a transparent ultraviolet curable resin such as a silicon resin and an epoxy resin and which is not cured, is in a liquid state. Thus, the thickness of the resin 50W is variable.

The stacked optical wafer 10W and the image pickup wafer 40W may be stacked in a state where the resin 50W having a predetermined thickness is disposed at at least one of the stacked optical wafer 10W or the image pickup wafer 40W, or the resin 50W may be injected between the stacked optical wafer 10W and the image pickup wafer 40W after the stacked optical wafer 10W and the image pickup wafer 40W are disposed at a predetermined interval.

<Step S40> Interval Adjustment Process

The interval between the optical member 10 and the image pickup member 40, that is, the thickness D50 of the resin 50 is adjusted so that the position of the image-forming plane FP measured in the measurement process S20 becomes the position of the light receiving surface 30SA. The thickness D50 of the resin 50 is adjusted so that a total value of the thickness D50 of the resin 50 and the thickness of the cover glass 20 becomes the length L.

Note that it goes without saying that in a case where the position of the image-forming plane FP measured in step S20 is corrected, the interval is adjusted on the basis of the corrected position of the image-forming plane FP.

<Step S50> Curing Process

The stacked optical wafer 10W and the image pickup wafer 40W are fixed in a state of the interval adjusted in the interval adjustment process S40 by the resin 50W being irradiated with ultraviolet light. Note that in a case where the resin 50W is an ultraviolet curable and thermoset resin, the resin 50W is further subjected to heat processing after ultraviolet irradiation.

Note that it is necessary to maintain relative positions of the stacked optical wafer 10W and the image pickup wafer 40W, that is, an interval, until curing of the resin 50W is completed. Thus, as the resin 50W, an ultraviolet curable resin or an ultraviolet curable and thermoset resin which is cured in a short time period is more preferable than a thermoset resin which requires time for curing.

In a case where the resin 50W shrinks through curing processing, the thickness of the resin 50W is preferably set so that the thickness after the curing processing becomes the interval between the optical member 10 and the image pickup member 40 in view of a shrinkage ratio of the resin 50W.

<Step S60> Separation Process

Figure 8:
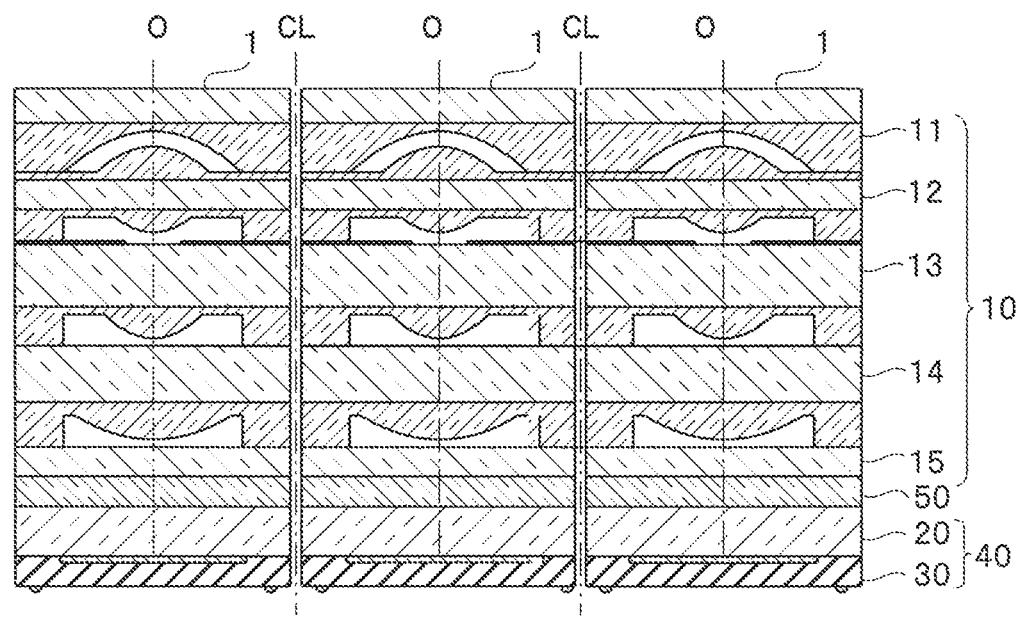
FIG. 8 is a cross-sectional diagram for explaining the manufacturing method of the image pickup apparatus for endoscope of the first embodiment.

As illustrated in FIG. 8, the bonded wafer 10W is separated into a plurality of image pickup apparatuses 1 by being cut along cut lines CL.

The separation process may be, for example, a cut process through laser dicing or a process of forming cutting grooves through sandblasting or etching.

According to the manufacturing method of the image pickup apparatus of the present embodiment, the optical member 10 is a wafer level optical member having the resin lens 11B, or the like, so that the optical member 10 is inexpensive and can be easily manufactured. Further, the position of the image-forming plane on which an object image, light of which is focused by the optical member 10, is formed matches the light receiving surface 40SA of the image pickup member 40, so that high performance can be achieved.

Further, the manufacturing method of the present embodiment includes the manufacturing process S10, the measurement process S20, the stacking process S30, the interval adjustment process S40 and the curing process S50 which are performed in a state of the stacked optical wafer 10W in which the optical wafers including the plurality of optical members 10 are stacked, and the image pickup wafer 40W including the plurality of image pickup members 40, and further includes the separation process S60 of cutting the bonded wafer 10W into a plurality of image pickup apparatuses 1 after the curing process S50.

As already described above, the plurality of optical members 10 included in one stacked optical wafer 10W have substantially the same length L from the exit surface 10SB to the image-forming plane FP. Thus, even if the measurement process S20, the stacking process S30, the interval adjustment process S40 and the curing process S50 are performed in a wafer state, a high-performance image pickup apparatus 1 can be obtained.

The manufacturing method of the image pickup apparatus of the present embodiment can collectively manufacture a plurality of image pickup apparatuses 1, so that it is possible to achieve high manufacturing efficiency and provide an inexpensive image pickup apparatus.

Modifications of First Embodiment

Image pickup apparatuses 1A and 1B of modifications 1 and 2 of the first embodiment, and modifications 1 and 2 of manufacturing methods of the image pickup apparatuses 1A and 1B will be described next. The image pickup apparatuses 1A and 1B and the manufacturing methods of the image pickup apparatuses 1A and 1B are similar to the image pickup apparatus 1 and the manufacturing method of the image pickup apparatus 1 and have the same functions, and thus, the same reference numerals will be assigned to components having the same functions and description will be omitted.

Modification 1 of First Embodiment

In the manufacturing method of the image pickup apparatus 1A of the present modification, a plurality of image pickup members 40 each including the cover glass 20 and the image pickup device 30 are manufactured in the manufacturing process S10. Meanwhile, the stacked optical wafer 10W in which a plurality of optical wafers 11W to 15W are stacked is manufactured. The measurement process S20 is performed on the stacked optical wafer 10W.

Figure 9:
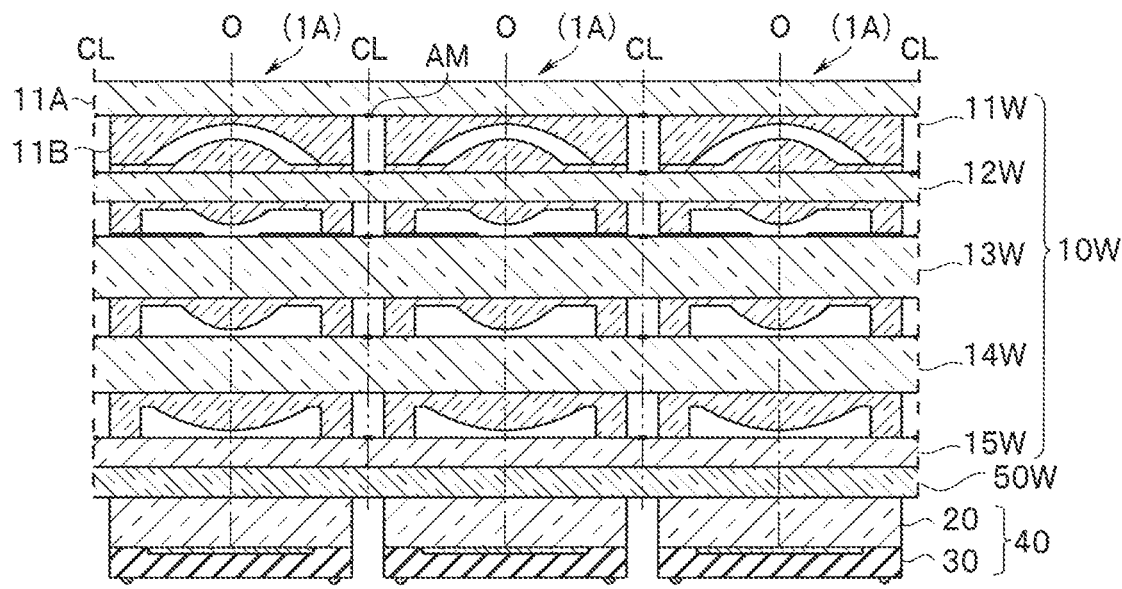
FIG. 9 is an exploded cross-sectional diagram of an image pickup apparatus for endoscope of modification 1 of the first embodiment.

Then, as illustrated in FIG. 9, the interval adjustment process S40 and the curing process S50 are performed on each of the plurality of image pickup members 40 and the stacked optical wafer 10W.

Note that, for example, a plurality of separated resin lenses 11B are disposed on the glass wafer 11AW in the optical wafer 11W. Alignment marks AM are disposed among the plurality of resin lenses 11B to manufacture a stacked optical wafer.

In a case where the image pickup wafer 40W is fixed on the stacked optical wafer 10W using the resin 50W, a defective image pickup apparatus is manufactured in a case where the image pickup wafer 40W includes a defective image pickup device 30.

The manufacturing method of the image pickup apparatus 1A has the effects of the manufacturing method of the image pickup apparatus 1, and further has an effect of a higher yield ratio than a yield ratio of the manufacturing method of the image pickup apparatus 1 because the image pickup apparatus 1A is manufactured using only the image pickup member 40 evaluated as a non-defective item. Further, the manufacturing method of the image pickup apparatus 1A enables manufacturing of an image pickup apparatus using commercially available image pickup members 40 which are separated into pieces or using image pickup members 40 with different specifications.

Modification 2 of First Embodiment

With the manufacturing method of the image pickup apparatus 1B of the present modification, the optical members 10 which are separated into pieces and the image pickup members 40 which are separated into pieces are manufactured in the manufacturing process S10.

Note that in a case where a plurality of optical members 10 which are separated into pieces from one stacked optical wafer 10W are used, the measurement process S20 may be performed on one of the plurality of optical members 10.

Figure 10:
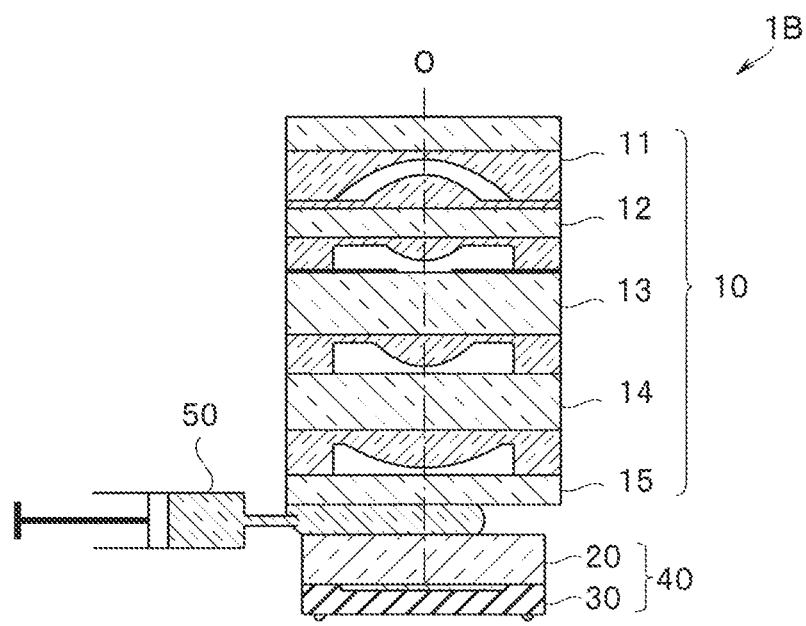
FIG. 10 is an exploded cross-sectional diagram of an image pickup apparatus for endoscope of modification 2 of the first embodiment.

As illustrated in FIG. 10, the interval adjustment process S40 and the curing process S50 are performed on one optical member 10 and one image pickup member 40. For example, in a state where an interval between the optical member 10 and the image pickup member 40 is adjusted to a predetermined interval L, the resin 50 is injected into a gap and curing processing is performed.

The manufacturing method of the image pickup apparatus 1B has the effects of the manufacturing method of the image pickup apparatus 1, and is further, particularly appropriate for a manufacturing method of an image pickup apparatus for endoscope which is a product of large item small scale production.

Second Embodiment

An image pickup apparatus 1C and a manufacturing method of the image pickup apparatus 1C of a second embodiment will be described next. The image pickup apparatus 1C and the manufacturing method of the image pickup apparatus 1C are similar to the image pickup apparatus 1 and the manufacturing method of the image pickup apparatus 1 and have the same functions, and thus, the same reference numerals will be assigned to components having the same functions, and description will be omitted.

Figure 11:
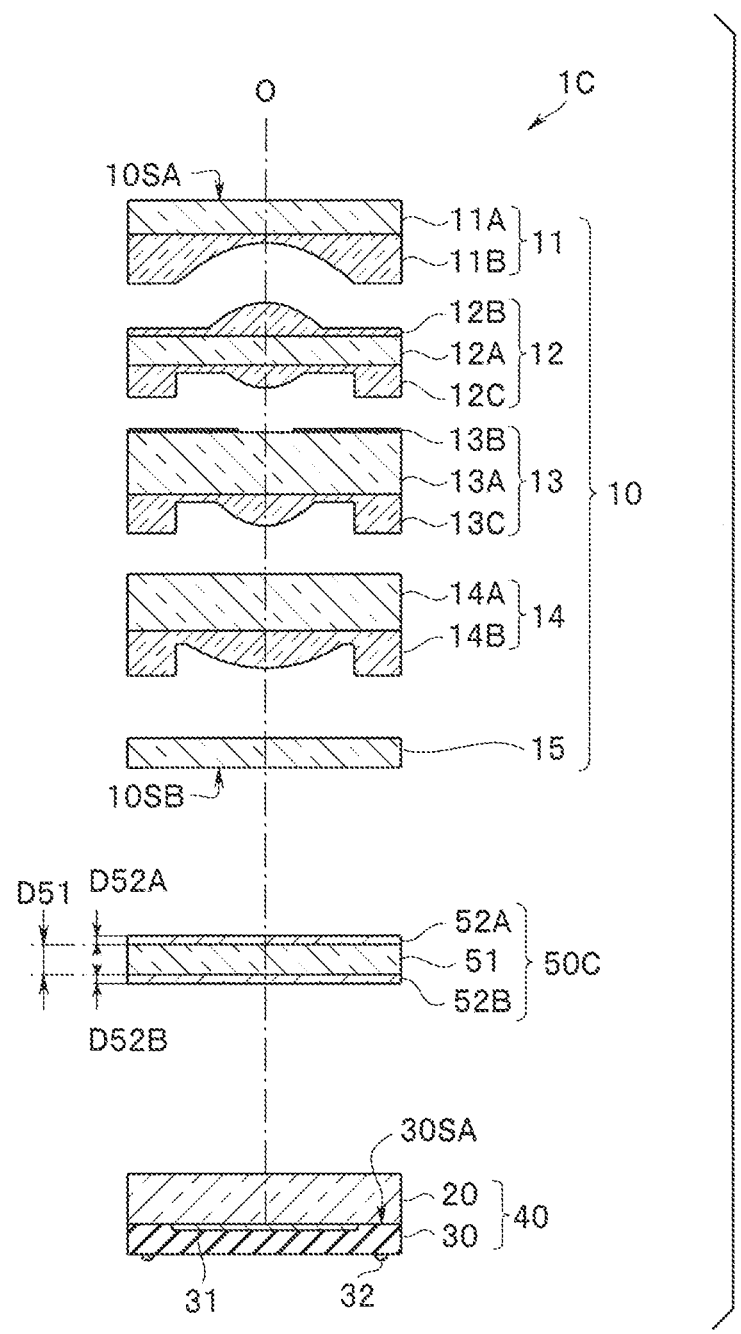
FIG. 11 is an exploded cross-sectional diagram of an image pickup apparatus for endoscope of a second embodiment.

As illustrated in FIG. 11, the image pickup apparatus 1C further includes a spacer 51 which roughly adjusts an optical path length, between the optical member 10 and the image pickup member 40. The spacer 51 is, for example, a glass plate having a thickness D51.

The optical member 10 is fixed to the spacer 51 by a transparent ultraviolet curable resin 52A disposed between the optical member 10 and the spacer 51. Meanwhile, the image pickup member 40 is fixed to the spacer 51 by a transparent ultraviolet curable resin 52B disposed between the image pickup member 40 and the spacer 51.

In a case where a length (interval) L between the optical member 10 and the image pickup member 40 is long, it is not easy to fill space only with the resin, and there is a case where distortion may occur, and optical characteristics may degrade. As a result of the image pickup apparatus 1C including the spacer 51, thicknesses of the resins 52A and 52B become thin. Thus, the image pickup apparatus 1C has the effects of the image pickup apparatus 1, and further, can be easily manufactured and has favorable optical characteristics.

Note that an optical path length D51 of the spacer 51 is preferably set slightly smaller than the length L on the basis of the position of the image-forming plane FP measured in the measurement process S20, that is, the length L, because such setting makes the thickness D52A of the resin 52A and the thickness D52B of the resin 52B thinner, facilitates manufacturing and leads to favorable optical characteristics.

Further, the optical path length D51 may be finely adjusted by the uncured resin 52B disposed between the image pickup member 40 and the spacer 51 after the optical member 10 is fixed to the spacer 51, or may be finely adjusted by the uncured resin 52A disposed between the optical member 10 and the spacer 51 after the image pickup member 40 is fixed to the spacer 51.

Modifications of Second Embodiment

Image pickup apparatuses 1D and 1E and manufacturing methods of the image pickup apparatuses 1D and 1E of modifications of the second embodiment will be described next. The image pickup apparatuses 1D and 1E and the manufacturing methods of the image pickup apparatuses 1D and 1E are similar to the image pickup apparatus 1 and the manufacturing method of the image pickup apparatus 1, and the like, and have the same functions, and thus, the same reference numerals will be assigned to components having the same functions, and description will be omitted.

Modification 1 of Second Embodiment

Figure 12:
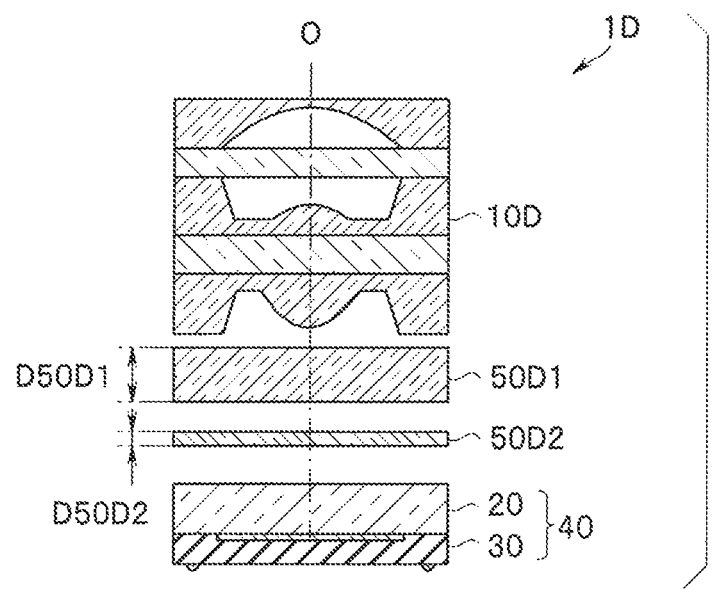
FIG. 12 is a cross-sectional diagram of an image pickup apparatus for endoscope of modification 1 of the second embodiment.

In the manufacturing method of the image pickup apparatus 1D of modification 1 of the second embodiment illustrated in FIG. 12, an interval between the optical member 10D and the image pickup member 40 is adjusted by a resin spacer 50D1 and a resin 50D2 in the interval adjustment process S40.

In a similar manner to the optical member 10, a plurality of hybrid optical devices are stacked in the optical member 10D.

The resin spacer 50D1 is manufactured in a similar manner to the lens 11, or the like, by applying a transparent resin, pressing a mold having a predetermined shape against the transparent resin, and curing the transparent resin by irradiating the transparent resin with ultraviolet (UV) light. In other words, the resin spacer 50D1 is molded.

A thickness D50D1 of the resin spacer 50D1 is set so that an optical path length including the resin spacer 50D1 becomes slightly smaller than the length L on the basis of the position of the image-forming plane FP measured in the measurement process S20, that is, the length L.

In the image pickup apparatus 1D, after the resin spacer 50D1 is disposed at the optical member 10E, an interval between the resin spacer 50D1 and the image pickup member 40 is finely adjusted to be the length L, and an uncured resin 50D2 is injected to a gap. The interval between the optical member 10D and the image pickup member 40 is fixed through curing processing of the resin 50D2. In other words, the length of the gap becomes the thickness D50D2 of the resin 50D2.

Modification 2 of Second Embodiment

Figure 13:
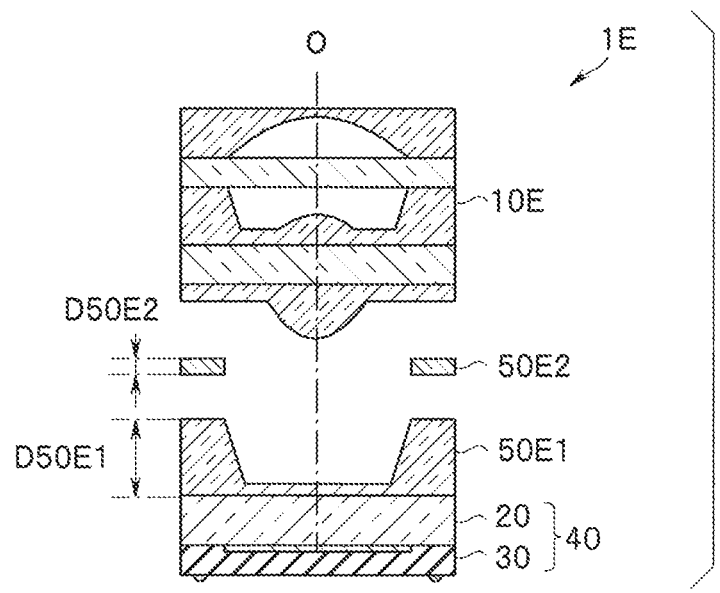
FIG. 13 is a cross-sectional diagram of an image pickup apparatus for endoscope of modification 2 of the second embodiment.

In the manufacturing method of the image pickup apparatus 1E of modification 2 of the second embodiment illustrated in FIG. 13, the interval between the optical member 10D and the image pickup member 40 is adjusted by a resin spacer 50E1 and a resin 50E2 in the interval adjustment process S40.

In a similar manner to the optical member 10, a plurality of hybrid optical devices are stacked in the optical member 10E.

The resin spacer 50E1 is molded in a similar manner to the resin spacer 50D1. After the resin spacer 50E1 having a thickness D50W1 is disposed at the image pickup member 40, an interval between the optical member 10D and the resin spacer 50E1 is finely adjusted. Then, the interval between the optical member 10E and the image pickup member 40 is fixed through curing processing of the resin 50E2 injected to the gap. In other words, a length of the gap becomes the thickness D50D2 of the resin 50E2.

Note that in place of the resin spacers 50D1 and 50E1, a resin spacer in which an optical path is space, which is formed with a transparent resin or an opaque resin, and which is molded may be used.

Third Embodiment

An image pickup apparatus 1F and a manufacturing method of the image pickup apparatus 1F of a third embodiment will be described next. The image pickup apparatus 1F and the manufacturing method of the image pickup apparatus 1F are similar to the image pickup apparatuses 1, 1A to 1E and the manufacturing methods of the image pickup apparatuses 1, 1A to 1E and have the same functions, and thus, the same reference numerals will be assigned to components having the same functions and description will be omitted.

Figure 14:
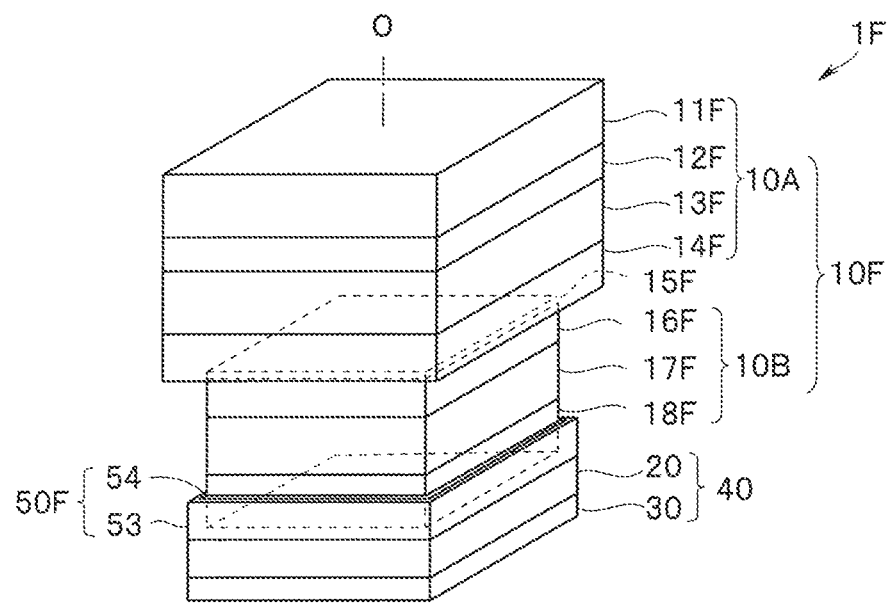
FIG. 14 is a perspective view of an image pickup apparatus for endoscope of a third embodiment.
Figure 15:
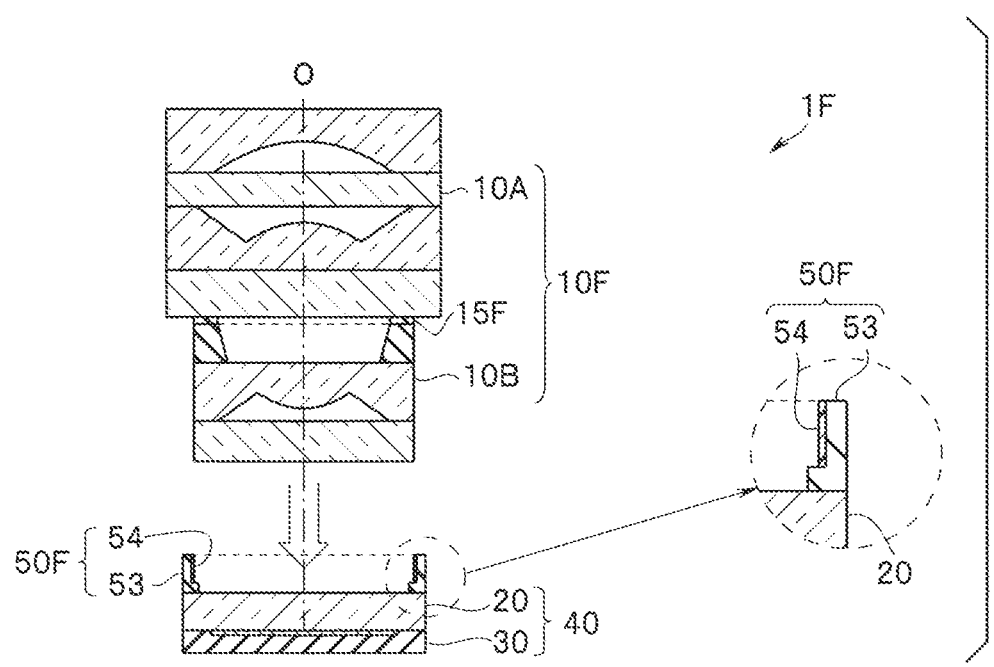
FIG. 15 is an exploded cross-sectional diagram for explaining a manufacturing method of the image pickup apparatus for endoscope of the third embodiment.

As illustrated in FIG. 14 and FIG. 15, an optical member 10F of the image pickup apparatus 1F includes a first optical member 10A and a second optical member 10B. The first optical member 10A includes a resin lens 11F, a glass plate 12F, a resin lens 13F and a glass plate 14F. The second optical member 10B includes a resin spacer 16F, a resin lens 17F and a glass plate 18F. The resin lens 11F, the resin lens 13F, the resin spacer 16F and the resin lens 17F are manufactured by cutting a molded resin wafer. The first optical member 10A is bonded to the second optical member 10B with a resin 15F.

A size of an entrance surface 10SA orthogonal to the optical axis O of the first optical member 10A having a rectangular parallelepiped shape is greater than a size of an exit surface 10SB orthogonal to the optical axis O of the second optical member 10B having a rectangular parallelepiped shape, and thus, the optical member 10F is a bright optical system which is capable of focusing more light on an object image.

A frame-like spacer 53 formed with, for example, silicon is disposed at the cover glass 20 of the image pickup member 40. The optical member 10F including the second optical member 10B inserted into the spacer 53 can move in an optical axis direction.

In the manufacturing method of the image pickup apparatus 1F, an interval between the optical member 10F and the image pickup member 40 is adjusted by the optical member 10F inserted into the spacer 53 moving in the optical axis direction in the interval adjustment process S40. Then, the interval between the optical member 10F and the image pickup member 40 is fixed by the resin 54 being subjected to curing processing.

The interval can be adjusted in a state where an optical axis of the optical member 10F matches an optical axis of the image pickup member 40, so that the image pickup apparatus 1F can be easily manufactured.

Note that a frame-like spacer may be disposed at the optical member 10F, and the interval between the optical member 10F and the image pickup member 40 may be adjusted by the image pickup member 40 inserted into the spacer moving in the optical axis direction.

In the image pickup apparatus 1F, the resin 54 which fixes the optical member 10F and the image pickup member 40 with the spacer 53 provided between the optical member 10F and the image pickup member 40 does not block an optical path, and thus, the resin 54 does not have to be a transparent resin, but is preferably an ultraviolet curable resin or an ultraviolet curable and thermoset resin which can be cured in a short time period. In a case where the spacer 53 is formed with a light blocking material, the resin 54 is preferably an ultraviolet curable and thermoset resin.

Further, it goes without saying that also in the manufacturing methods of the image pickup apparatuses 1C and 1F, the interval adjustment process S40, and the like, is performed in a state of the stacked optical wafer 10W and the image pickup wafer 40W in a similar manner to the manufacturing methods of the image pickup apparatuses 1 and 1A.

Further, it goes without saying that endoscopes 9A to 9F including the image pickup apparatuses 1A to 1F have the effects of the endoscope 9, and further respectively have the effects of the image pickup apparatuses 1A to 1F.

The present invention is not limited to the above-described embodiments and the like, and various changes, combinations and application are possible within a range not deviating from the gist of the invention.

What is claimed is:

1. A manufacturing method of an image pickup apparatus for use with an endoscope, the manufacturing method comprising:
    measuring a position of an image-forming plane on which an object image, light of which is focused by an optical member having a plurality of stacked optical devices, is formed;
    stacking the optical member and an image pickup sensor having a light receiving surface in an optical axis direction such that a space having a first thickness in the optical axis direction is provided between the optical member and the light receiving surface;
    applying an uncured transparent resin to the space to provide an uncured transparent resin layer having the first thickness;
    adjusting the first thickness to a second thickness, different from the first thickness, so that the light receiving surface is positioned at the measured image-forming plane; and
    subsequent to the adjusting, curing the uncured transparent resin layer to fix the optical member and the light receiving surface separated by the second thickness.

2. The manufacturing method according to claim 1, wherein the uncured transparent resin is an ultraviolet curable resin or an ultraviolet curable and thermoset resin.

3. The manufacturing method according to claim 1, wherein the uncured transparent resin layer includes a spacer having a thickness less than the second thickness.

4. The manufacturing method according to claim 3, wherein an optical path length of the spacer is set based on the measured position of the image-forming plane.

5. The manufacturing method according to claim 1, wherein the first thickness is adjusted to the second thickness by moving one or more of the optical member or the image pickup sensor in an optical axis direction.

6. The manufacturing method according to claim 1, further comprising, subsequent to the curing, cutting an optical wafer having a plurality of the optical members and an image pickup wafer having a plurality of the image pickup sensors into a corresponding plurality of image pickup apparatuses.

7. The manufacturing method according to claim 1, wherein the measuring is performed on an optical wafer having a plurality of stacked optical members, and the adjusting and the curing are performed on the optical wafer together with a stacked image wafer having a plurality of corresponding image pickup sensors.

8. The manufacturing method according to claim 1, further comprising:
    prior to the measuring, manufacturing the optical member by stacking the plurality of optical devices;
    wherein at least one of the plurality of optical devices includes a resin lens formed using a mold.

9. The manufacturing method according to claim 1, wherein the measuring comprises measuring a length from an exit surface of the optical member to the image-forming plane.

10. A manufacturing method of an image pickup apparatus for use with an endoscope, the manufacturing method comprising:
    manufacturing an optical member in which a plurality of optical devices are stacked and an image pickup sensor having a light receiving surface;
    measuring a position of an image-forming plane on which an object image, light of which is focused by the optical member, is formed;
    stacking the optical member and the image pickup sensor;
    adjusting an interval between the optical member and the image pickup sensor so that a measured position of the image-forming plane becomes a position of the light receiving surface; and
    fixing the optical member and the image pickup sensor in a state of the adjusted interval by performing curing processing on a transparent resin disposed to fill an optical path between the optical member and the image pickup sensor,
    wherein at least one of the optical member or the image pickup sensor is fixed to a spacer with the transparent resin disposed between the optical member or the image pickup sensor and the spacer is configured to roughly adjust an optical path length in curing processing, the optical path is set on a basis of the measured position of the image-forming plane.

11. The manufacturing method according to claim 10, wherein the interval is adjusted by moving one or more of the optical member or the image pickup sensor in an optical axis direction.

12. The manufacturing method according to claim 10, further comprising, subsequent to the curing, cutting an optical wafer having a plurality of the optical members and an image pickup wafer having a plurality of the image pickup sensors into a corresponding plurality of image pickup apparatuses.

13. The manufacturing method according to claim 10, wherein the measuring comprises measuring a length from an exit surface of the optical member to the image-forming plane.

14. The manufacturing method according to claim 10, wherein the uncured transparent resin is an ultraviolet curable resin or an ultraviolet curable and thermoset resin.

15. The manufacturing method according to claim 10, wherein the measuring is performed on an optical wafer having a plurality of stacked optical members, and the adjusting and the curing are performed on the optical wafer together with a stacked image wafer having a plurality of corresponding image pickup sensors.

16. The manufacturing method according to claim 10, further comprising:
   prior to the measuring, manufacturing the optical member by stacking the plurality of optical devices;
   wherein at least one of the plurality of optical devices includes a resin lens formed using a mold.

* * * * *